United States Patent
Patton et al.

[11] Patent Number: 5,377,667
[45] Date of Patent: Jan. 3, 1995

[54] SPECULUM FOR DILATING A BODY CAVITY

[75] Inventors: Michael T. Patton, 6315 Central City Blvd. #513, Galveston, Tex. 77551; Howard K. Wallace, Gainesville, Fla.

[73] Assignee: Michael T. Patton, Galveston, Tex.

[21] Appl. No.: 985,047

[22] Filed: Dec. 3, 1992

[51] Int. Cl.[6] ............................................. A61B 7/02
[52] U.S. Cl. ............................................ 128/3; 128/20
[58] Field of Search ................... 128/3, 17, 18, 19, 12, 128/20, 5

[56] References Cited

U.S. PATENT DOCUMENTS

| | | | |
|---|---|---|---|
| 350,721 | 10/1886 | Cooper | 128/17 |
| 365,969 | 7/1887 | Collins | 604/105 |
| 380,745 | 4/1888 | Chamberlin | 128/17 |
| 708,452 | 9/1902 | Beist | 604/109 |
| 832,201 | 10/1906 | Kistler | 604/108 |
| 2,083,573 | 6/1937 | Morgan | 128/3 |
| 2,545,201 | 3/1951 | Gilbert | 128/17 |
| 3,568,665 | 3/1971 | Lundgren | 128/17 |
| 3,702,606 | 11/1972 | Barnard | 128/17 |
| 3,985,125 | 10/1976 | Rose | 128/17 |
| 4,010,740 | 3/1977 | Littorin | 128/17 |
| 4,130,113 | 12/1978 | Graham | 128/20 |
| 4,350,151 | 9/1982 | Scott | 128/17 |
| 4,385,626 | 5/1983 | Danz | 128/17 |
| 4,597,382 | 7/1986 | Perez, Jr. | 128/17 |
| 4,807,600 | 2/1989 | Hayes | 128/17 |
| 5,007,409 | 4/1991 | Pope | 128/17 |

FOREIGN PATENT DOCUMENTS

| | | | |
|---|---|---|---|
| 542744 | 8/1922 | France | 128/3 |
| 1273135 | 3/1966 | Germany . | |
| 391204 | 4/1933 | United Kingdom | 128/3 |

OTHER PUBLICATIONS

"Euro-Med/Cooper Surgical Catalog," Winter/Spring 1992.

*Primary Examiner*—Richard J. Apley
*Assistant Examiner*—Beverly A. Meindl

[57] ABSTRACT

A speculum for dilating a body cavity includes a base and a number of arms pivotably attached to the base. There is an actuator movably attached to the base for causing each of the arms to move relative to each other from a closed position to an opened position so that a body cavity can be smoothly opened after the arms have been inserted into the body cavity.

31 Claims, 5 Drawing Sheets

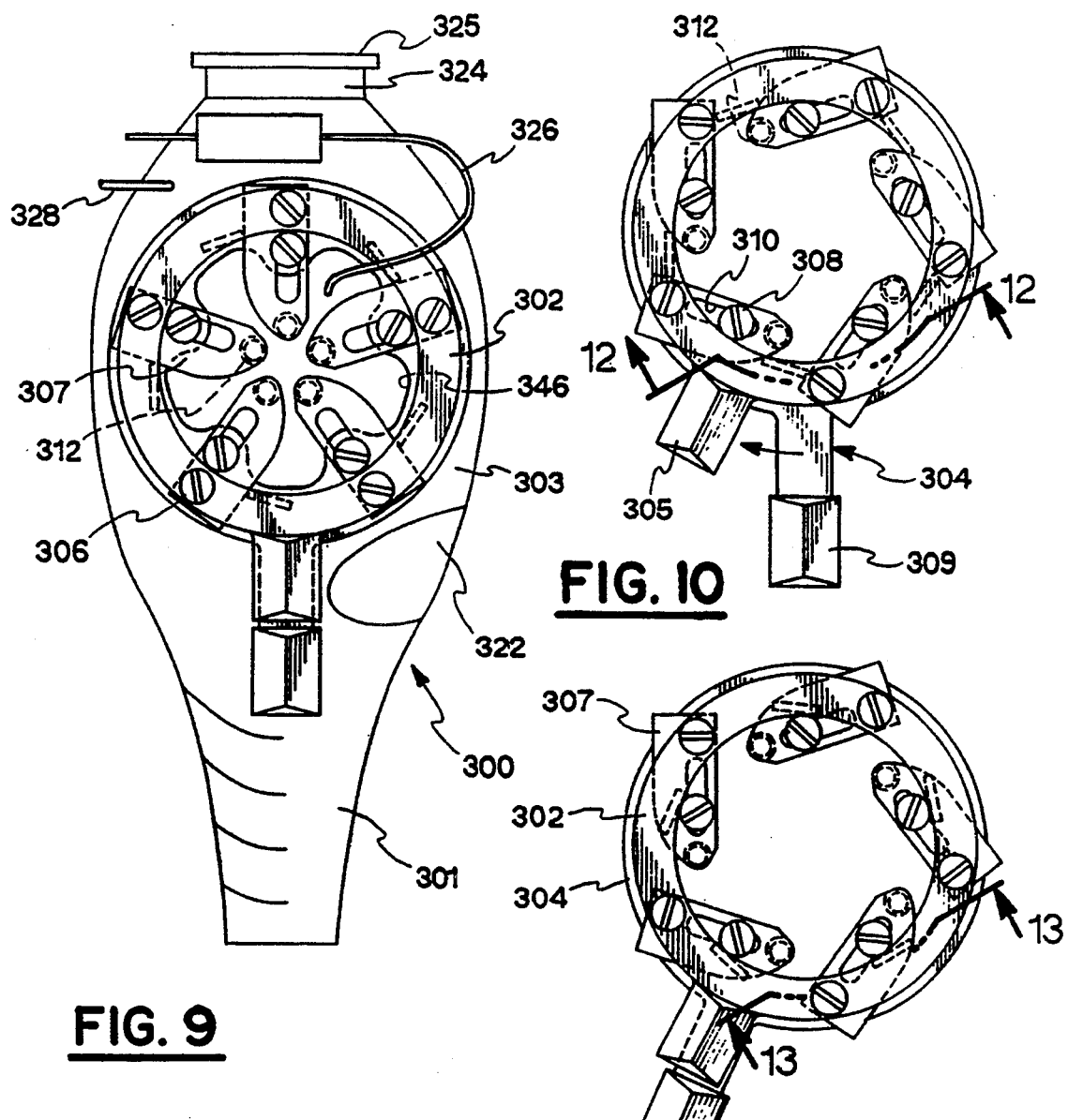
FIG. 9
FIG. 10
FIG. 11
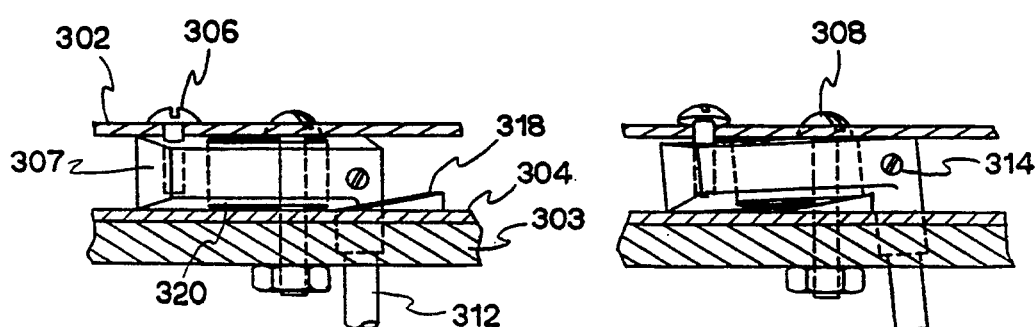
FIG. 12
FIG. 13

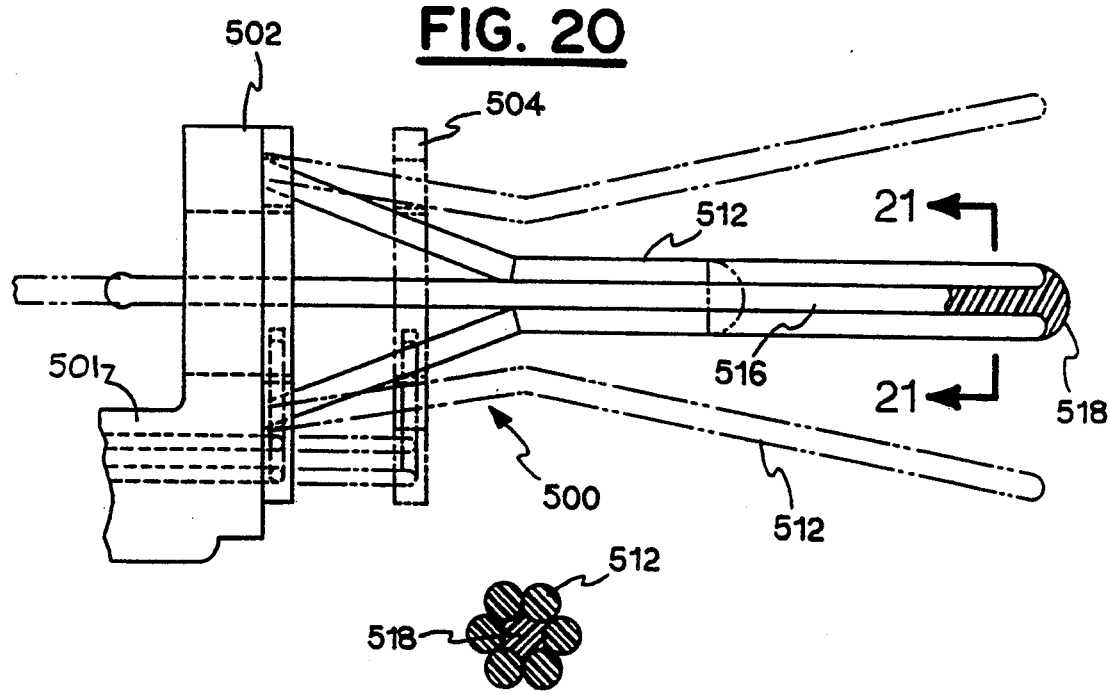
FIG. 20
FIG. 21
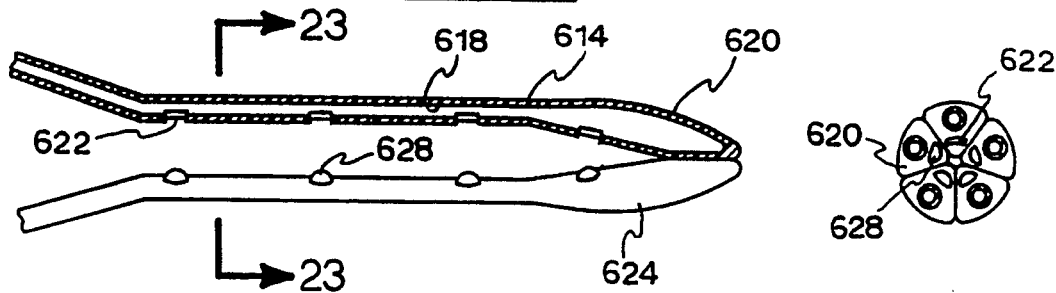
FIG. 22
FIG. 23

SPECULUM FOR DILATING A BODY CAVITY

FIELD OF THE INVENTION

The present invention relates to a device for dilating a body cavity.

BACKGROUND OF THE INVENTION

Traditional devices for dilating body cavities include medical or surgical instruments known as specula, dilators, or retractors.

A conventional speculum is used to enlarge an existing body cavity, such as during vaginal or rectal examinations. Such dilators are traditionally made of surgical steel which may be sterilized after the examination of each patent.

A drawback of steel devices is that they tend to feel cold when contacting the human tissue which is spread apart during examination or surgery. Typical examinations of body orifices such as described above are anxiety producing. Accordingly, the added shock of a cold surgical instrument against the tissue of the patient heightens the anxiousness of the patient. Furthermore, anxious patients may have more tightly tensed muscles which impede the spreading open of the cavity. The physical examination is thus hampered and slowed.

Physicians using traditional specula often must compromise patient comfort to achieve a clear view of the cervix. When patient comfort is a priority as with younger patients, the field of view must be compromised. Physician compromise by simply varying the width of the traditional speculum blades.

Furthermore, conventional steel dilators must be sterilized after each use to prevent cross-contamination between patients. Such sterilization is time-consuming, costly, and requires that the physician have multiple instruments available so that a sterilized dilator is at hand while the other dilators are being cleaned between uses.

U.S. Pat. No. 4,807,600 to Hayes discloses a speculum protector which is essentially a disposable cover for blades of a reusable speculum. The speculum disclosed in Hayes is a traditional duck bill speculum having two opposed concavo-convex blades movable outwardly relative to each other and is particularly suited for vaginal examinations.

It is also known to place the cut off finger of a surgical glove or a condom over the blades of a steel dilator. As with the features of the above-described Hayes speculum protector, these plastic coverings for preventing contamination of the instrument are satisfactory. However, given the heightened awareness of the virility and virulence of sexually transmitted diseases and the cost of sterilizing surgical instruments even on an occasional basis, there is a need for a dilator which provides a more consistent, better solution to the problem of disease transmission.

U.S. Pat. No. 3,702,606 to Barnard discloses a duck bill speculum injection molded from a plastic such as PERSPEX TM.

U.S. Pat. No. 350,721 to Cooper discloses a speculum having three elongated arms, one of which is made integral with a cross-bar for moving the other two arms outwardly as it is moved.

U.S. Pat. No. 2,083,573 to Morgan discloses a speculum having four elongated blades, a main object of which is to provide for parallel movement of the blades during both divergence and convergence thereof. Although arcuate paths of the blades are possible when the blades are moved outwardly, Morgan intends that in actual practice the operator manipulates the handles so as to cause blade movement along radii.

German Auslegeschrift 1,273,135 to Melanovsky dated Jul. 18, 1968, discloses a cervical dilator having expander arms movable radially outwardly by means of an adjusting disk with spiral grooves meshing with guide members associated with the expander arms. Although the configuration of the Melanovsky grooves is intended to afford a self-locking action for maintaining the expander arms in the desired position, the dilator is unsuited for one-handed operation.

OBJECTS AND SUMMARY OF THE INVENTION

According, it is an object of the invention to provide a dilator which overcomes the drawbacks of the known devices.

It is a further object of the invention to provide a dilator which is simple to use, and which eliminates the anguish and possible psychological trauma caused by conventional dilators during gynecological procedures.

It is still further object of the invention to provide a dilator which has a smaller spreader width in its closed position for reducing physical and mental trauma resulting from the excessive width of known dilators.

It is yet another object of the invention to provide a dilator which can be easily and accurately manipulated by the use of one hand.

It is a still further object of the invention to provide a dilator which is easier to insert and more safely inserted in body cavities than known dilators.

It is a further object of the invention to provide a dilator which is less expensive to use than conventional dilators.

It is yet another object of the invention to provide a dilator which is self-retaining in an orifice of the body, such as the vagina.

It is another object of the invention to provide a dilator which provides the user with a better view of a body cavity for enhanced physical examination of the patient, without compromising patient comfort.

It is yet another object of the invention to provide a dilator which eliminates the need of using additional retractors, such as a lateral vaginal retractor (LVR), or condoms in conjunction with the dilator arms to ensure adequate spreading of the body cavity.

It is another object of the invention to provide a dilator having tissue-spreading arms which do not pinch the tissue of the body as the arms are converging when the dilator is moved from an open position to a closed position, and when the dilator is moved from a closed position to an open position.

A further object of the invention is to provide a dilator suited for use with other surgical instruments.

A yet still further object of the invention is to provide a dilator which retains the body cavity in an open position for an extended period of time without discomfort to the patient and without damaging the surrounding body tissue.

In summary, the present invention provides a dilator which achieves these and other objects.

A preferred embodiment of the invention provides a dilator having a base and a plurality of arms pivotably attached to the base. An actuator plate is disposed adjacent to and movable relative to the base, and includes a member for engaging each of the arms for moving them relative to each other from a closed position to an open position for dilating a body cavity.

Another preferred embodiment of the invention is a dilator comprising a base, a plurality of arms pivotably and rotatably attached to the base, and a member for pivoting and rotating each of the arms relative to each other for moving the arms from a closed position to an open position by which a body cavity is dilated.

BRIEF DESCRIPTION OF THE DRAWINGS

FIG. 9 is a rear elevational view of still another preferred embodiment of the dilator according to the invention, shown in its closed position;

FIG. 10 is a rear elevational view of portion of the embodiment of FIG. 9, showing the dilator in its open position;

FIG. 11 is a view similar to FIG. 10, showing the preferred embodiment of the dilator of FIG. 9 in its open and flared position;

FIG. 12 is a fragmentary, sectional view taken along line 12—12 of FIG. 10, on an enlarged scale;

FIG. 13 is a fragmentary, sectional view taken along line 13—13 of FIG. 11, on an enlarged scale;

FIG. 20 is a schematic, side elevational view of a preferred embodiment of an insertion rod being used with a dilator according to the invention;

FIG. 21 is a sectional view of the insertion rod taken along line 21—21 of FIG. 20, on an enlarged scale;

FIG. 22 is a side elevational view partially in section, of yet another preferred embodiment of dilator blades according to the present invention; and FIG. 23 is a sectional view taken along line 23—23 of FIG. 22.

DETAILED DESCRIPTION OF THE INVENTION

FIGS. 1–4

Figure 1:
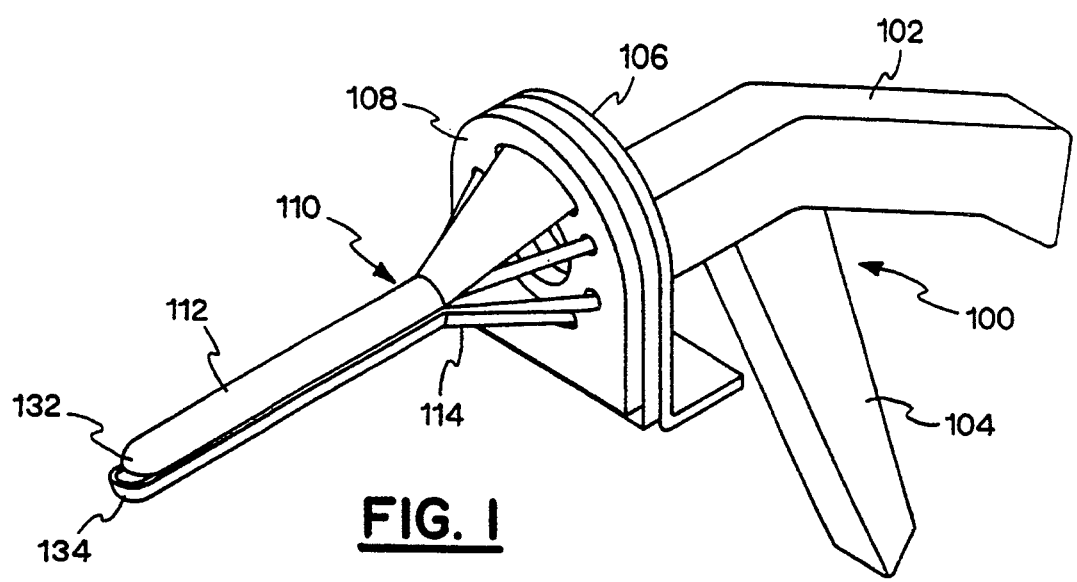
FIG. 1 is a perspective view of one of the preferred embodiments of the invention in a closed position.

A dilator 100 having a fixed handle 102 and a movable handle 104 operably attached thereto is shown in a closed position in FIG. 1.

Figure 2:
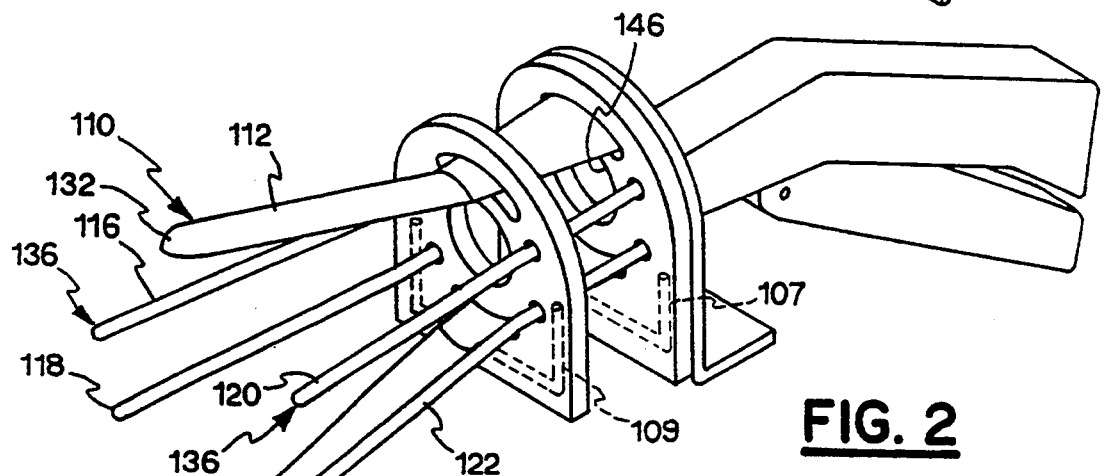
FIG. 2 is a perspective view of the embodiment of FIG. 1 in an open position.
Figure 3:
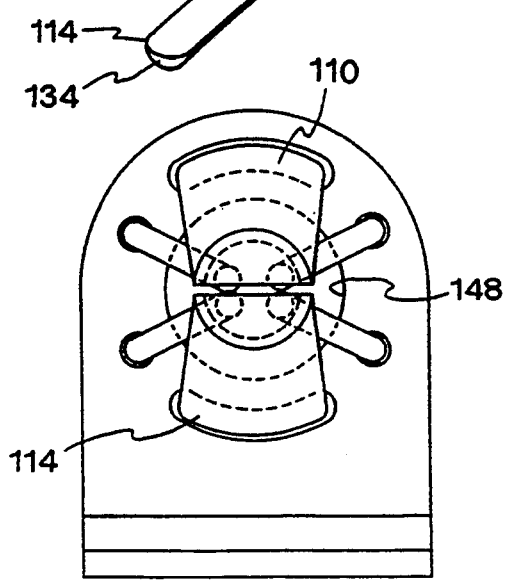
FIG. 3 is a front elevational view of the preferred embodiment of FIG. 1.
Figure 4:
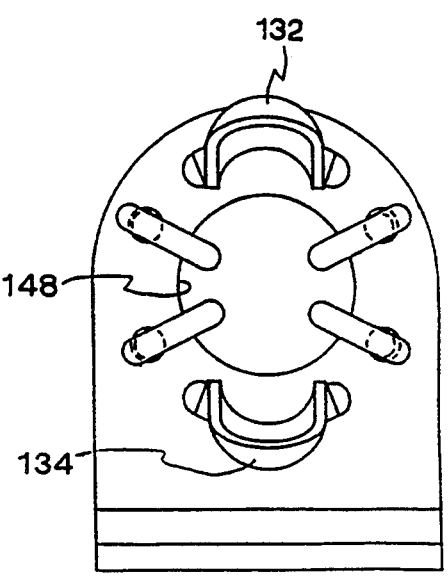
FIG. 4 is a front elevational view of the open position of the dilator shown in FIG. 2.

A fixed base 106 is attached to handle 102 by means of an anchor member 107 or by being integrally formed therewith. A movable base plate 108 is disposed adjacent fixed base 106 when dilator 100 is in its closed position. An actuating member 109 is operably disposed between movable base plate 108 and movable handle 104 so that movable base plate 108 moves away from base 106 when movable handle 104 is brought closer to fixed handle 102, as shown in FIG. 2.

A plurality of dilator arms 110 extend through movable base plate 108 and are attached to base 106. An upper concavo-convex dilator blade 112 is disposed above a lower dilator blade 114, both of which being movably attached to base 106. Likewise, a pair of right side dilator rods 116, 118, as well as a pair of left side dilator rods 120, 122, are located respectively between upper dilator blade 112 and lower dilator blade 114. Tips 132, 134 of upper and lower dilator blades 112, 114, respectively, substantially enclose tips 136 of dilator rods 116, 118, 120, and 122 when dilator 100 is in its closed position.

An examination window 146 is defined in base plate 106. A corresponding examination window 148 extends through movable base plate 108.

FIGS. 5–8

Figure 5:
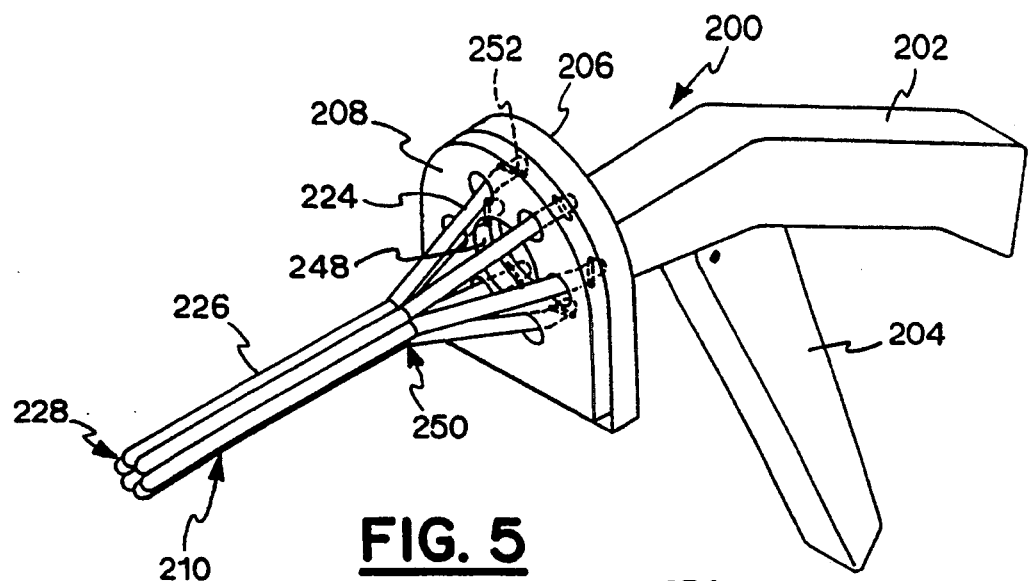
FIG. 5 is a perspective view of another preferred embodiment of the invention in its closed position.

A dilator 200 having a fixed handle 202 and a movable handle 204 operably attached thereto is shown in a closed position in FIG. 5. A fixed base 206 is removably attached to handle 202 by means of an anchor member 207 or is integrally formed therewith.

Figure 6:
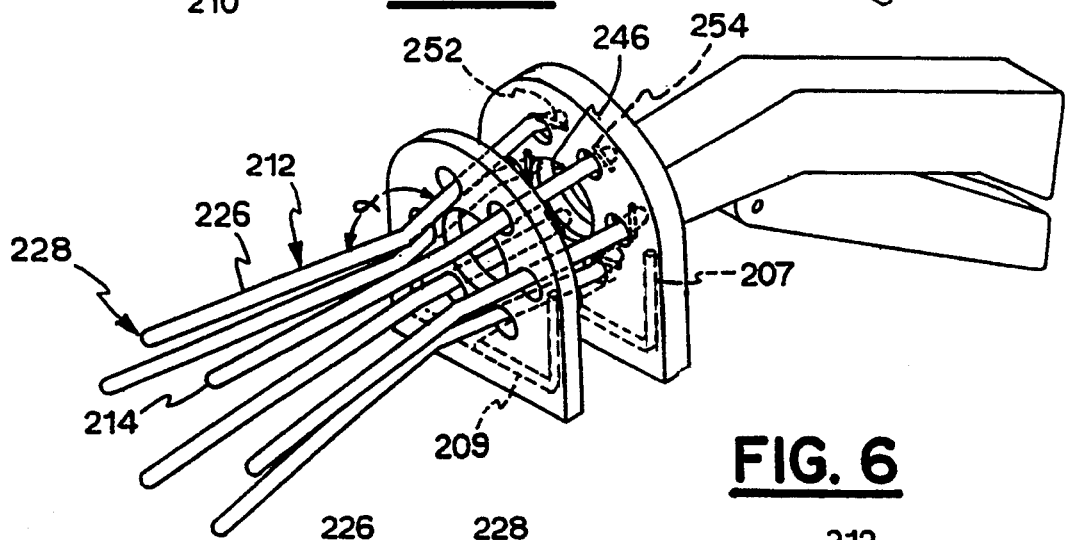
FIG. 6 is a perspective view of the embodiment of FIG. 5 shown in an open position.

A base plate 208 is disposed adjacent fixed base 206 when dilator 200 is in its closed position. An actuating member 209 is operably disposed between movable base plate 208 and movable handle 204 so that base plate 208 moves relative to base 206 when movable handle 204 is squeezed and brought closer to fixed handle 202, as shown in FIG. 6. A plurality of dilator arms 210 extend through movable base plate 208 and are pivotably attached to base 206.

Individual dilator arms or rods 212, 214, 216, 218, 220, and 222 collectively define a hexagonal shape as will be appreciated from the description of the OPERATION, below.

Each dilator rod 212 has a pivoted end 224 and a free end 226. An insertion tip 228 is defined at the outermost end of dilator rods 212. An area 250 generally indicates the points at which there is a change of curvature in dilator rods 212 between pivoted end 224 and free end 226.

Preferably, an angle $\alpha$ disposed between pivoted end 224 and free end 226 is less than 180°. This angled construction of dilator rod 212, and, preferably, the other dilator rods 214, 216, 218, 220 and 222 enhances the operation of dilator 200 in opening particular body cavities, as will be described in greater detail below under OPERATION of the invention.

As in the previous embodiment, an examination window 246 is defined in base plate 206. A corresponding examination window 248 extends through movable base plate 208.

FIGS. 9–13

FIG. 9 illustrates a further preferred embodiment of a dilator according to the invention.

A handle 301 extends from a main body 303. In order to control the size of the "window" or "iris" through which the user looks into a body cavity during use, an iris diameter control disk is movably attached to main body 303.

An arm flare control disk 304 is movably attached to main body 303 so as to provide for additional control over the manner in which the body cavity is dilated. A pivot screw 306 secures a tiltable rotating arm 307 to iris diameter control disk 302. A slot guide screw 308 extends through a guide slot 310 defined in rotating arm 307.

A plurality of dilator arms 312, five of which are preferably used in this embodiment, are removably attached to respective ones of rotating arms 307 by means of set screws 314.

A flare wedge 318 is provided on arm flare control disk 304. Flare wedge 318 is configured for cooperating with a mating surface 320 defined on rotating arm 307 in order to cause dilator arms 312 to move radially outwardly; i.e., to flare out, as will be described in greater details under OPERATION below.

Additional features of the invention that may be provided include a contoured portion 322 such as for receiving a thumb or other finger of a user's hand, and a hinge 324 to which an optional magnifying glass 325 can be rotatably attached for movement between the illustrated substantially horizontal position to a downwardly extending position as viewed in FIG. 9 (not shown) in front of examination window 346 extending through main body 303. In the non-use, stored position, magnifying glass 325 rests substantially horizontally as shown in FIG. 9.

A fiber optic light rod 326 is attached to main body 303 for providing illumination inside the body cavity by directing light from a light source (not shown).

Furthermore, a smoke evacuator tube 328 is provided for removing smoke generated during laser surgery procedures, for example.

FIGS. 14–19

A further preferred embodiment of a dilator 400 according to the invention is shown in FIGS. 14–19 with the majority of its main body 401, which may be constructed similar to those of the other embodiments, omitted for clarity.

An iris diameter control disk 402 is movably attached to main body 401 and movably attached relative to an arm flare control disk 404. A lever 405 for actuating iris diameter control disk 402 is joined thereto.

In a similar manner, a lever 407 extends from arm flare control disk 404. A guide screw 408 attached to an extension 409 is received in a guide slot 410 defined in iris diameter control disk 402. A dilator arm 412 extends from its respective extension 409 and is removably attached thereto by a set screw 414.

Figure 19:
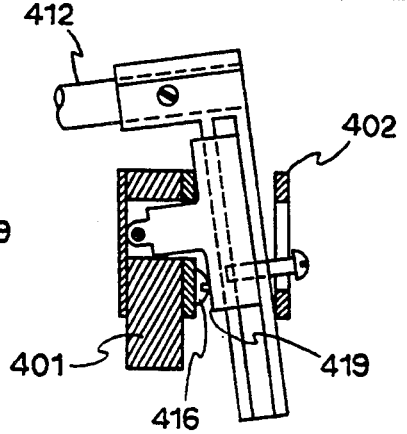
FIG. 19 is a fragmentary, sectional view taken along line 19—19 of FIG. 18, on an enlarged scale.

To provide the desired flaring out of dilator arms 412 when dilator 400 is in use, a flare screw 416 extending through arm flare control disk 404 into main body 401 is provided. A guide member 418 engages flare screw 416 and provides the desired flare, specifically by the engagement of an inner surface 419 with the head of flare screw 416, as best seen in FIG. 19. A pivot screw 420 rotatably attaches guide member 418 to main body 401.

As best understood from a consideration of the succession of FIGS. 14, 16, 18 and FIGS. 15, 17, 19, respectively, extension 409 is slidable relative to guide member 418.

FIGS. 20–23

Additional variations of preferred constructions of the dilator and the dilator arms according to the invention that are usable with all the above-described preferred embodiments are shown in FIGS. 20–23.

FIGS. 20–21 schematically illustrates a dilator 500 having a fixed base 502 and a movable member 504 for opening and closing dilator arms 512. Fixed base 502 is integrally molded with a handle portion 501.

A single, removable insertion rod 516 is disposed centrally of the plurality of dilator rods 512 and includes a blunt, somewhat hemispherical insertion tip 518 for providing a unified insertion tip which is especially suited for adolescent and virginal patients. Hemispherical tip 518 is withdrawn rearwardly (i.e., to the left as viewed in FIG. 20) after dilator arms 512 have been moved radially outwardly by movably member 504. Tip 518 can be made of sufficiently soft material that it is possible to withdraw insertion rod 516 even when dilator arms 512 are in a closed position.

Turning to FIGS. 22 and 23, a dilator arm 614 particularly suited for use in procedures involving laser surgery is shown. Laser surgery and other types of cauterizing operations, produce smoke and water vapor when the tissue is burned. A hollow passage 618 extending from a tip 620 rearwardly carries smoke drawn through one or more of a plurality of openings 622 by means of a negative pressure (i.e., a vacuum source, not shown). A dilator arm 624 according to a further embodiment may be hollow or solid, and includes one or more windows 628 for transmitting light into a body cavity from an external light source (not shown). For enhanced light transmission, dilator arm 624 may be made of a suitable synthetic material having appropriate light-carrying characteristics. When five dilator arms are used, such as one arm 614 in conjunction with four arms 624, lots of light is provided via windows 628 while evacuating smoke through openings 622.

OPERATION

In use, dilator 100 of FIGS. 1–4 is manipulated by the operator, such as a gynecologist or proctologist, holding onto fixed handle 102 with one hand.

In the case where handles 102, 104 are reusable, sterilizable metal handles, and the remaining parts are one-time use components intended to be discarded after contacting each patient, a plastic sheath may be placed over handles 102, 104 to provide additional protection against contamination.

Once the cervix has been located by tips 132, 134 then the operator squeezes movable handle 104 to bring it closer to handle 102, thereby shifting actuating member 109 and, hence, movable base plate 108 forwardly. The forward movement of base plate 108 away from fixed base 106 causes dilator blades 112, 114 as well as dilator rods 116, 118, 120, and 122 to move radially outwardly away from each other, thereby spreading the tissue.

Dilator 200, illustrated in FIGS. 5–8, is used in a manner similar to the embodiment of FIG. 1.

The six dilator arms 210 configured as individual dilator rods 212–222, are particularly suited for rectal examinations and for gynecological examinations of younger patients and with patients having narrow vaginas.

Figures 7, 8:
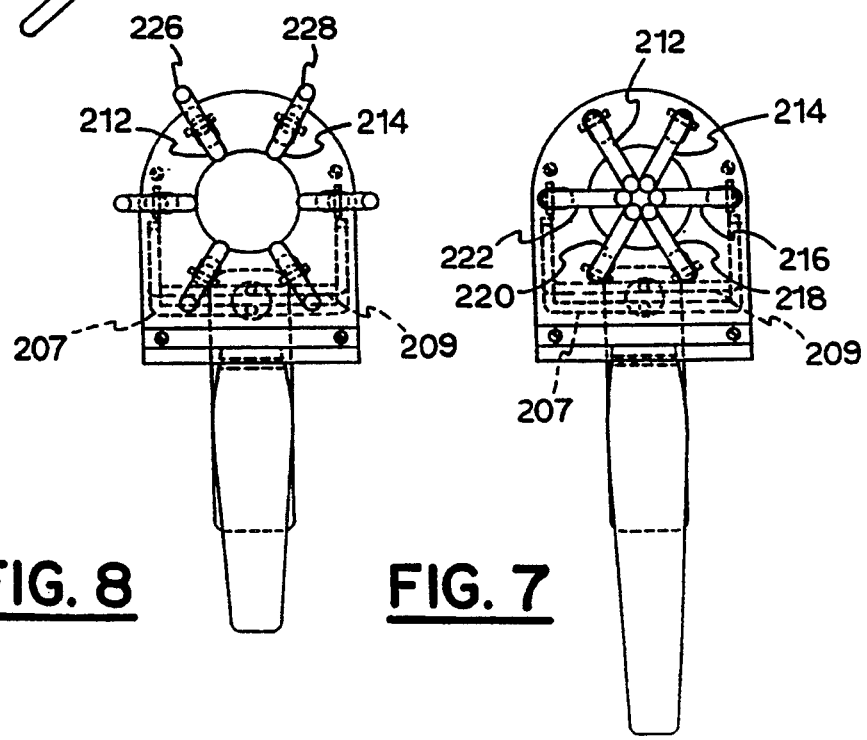
FIG. 7 is a front elevational view of the preferred embodiment of FIG. 5 in its closed position.
FIG. 8 is a front elevational view of the preferred embodiment of FIG. 5 showing the open position of FIG. 6.

As best appreciated from considering FIG. 7, the hexagonal configuration of free ends 228 of the individual dilator rods is oriented so that flat sides of the thus-defined hexagon extend substantially horizontally. Thus, during outward movement of dilator arm 210 when movable handle 204 is rotated toward fixed handle 202, for dilating the body cavity, no unnecessary pressure is placed upon the urethral passage or rectum. Visual inspection of the body cavity by the physician is possible by looking over handle 202 through window 246.

In order to use the further preferred embodiment of dilator 300 according to the invention, as shown in FIGS. 9–13, one grasps handle 301, depicted for a right handed user, and places the thumb or other desired finger in contoured portion 322.

When the operator rotates actuating lever 305 clockwise from its position shown in FIG. 9 to the open position shown in FIG. 10, the iris diameter (i.e., the size of the "window" through which the operator looks) and the size of dilation of the body cavity increases.

Given guide slot 310 and slot guide screw 308, it will be appreciated that movement of rotating arm 307 resulting from rotation of iris diameter control disk 302 causes dilator arms 312 to rotate in space as dilator arms 312 move radially outwardly. This radially outwardly spiraling motion of dilator arms 312 is especially desirable when dilator arms 312 are being moved from an open to a closed position and from a closed position to an open position. In other words, a smooth, "rolling" movement of dilator arms 312 relative to the tissue of the body cavity essentially eliminates undesirable pinching of the body tissue between adjacent ones of dilator arms 312. Thus, a more comfortable and less physically and psychologically damaging examination of the body cavity results.

In the case of a vaginal examination, for example, actuating lever 309 will likewise be rotated clockwise from the position shown in FIGS. 9 and 10 to the position illustrated in FIG. 11.

Accordingly, arm flare control disk 304 is moved clockwise, whereby flare wedge 318 contacts mating surface 320 of rotating arm 307. This engagement of flare wedge 318 with arm 307 causes arm 307 and, hence, dilator arm 312 to move from the position shown in FIG. 12 to the outwardly flared position illustrated in FIG. 13. When dilator arms 312 are thus flared (i.e., diverged) a substantially conical opening of the vaginal cavity is provided in the posterior thereof, while in the anterior portion of the cavity, a less enlarged, somewhat pentagonal opening is provided.

The more pronounced outward flaring of the free ends of dilator arms 312 not only provides an enhanced larger view of the cervix, but the conical flaring of dilator arms 312 causes dilator 300 to be self-retaining within the body cavity. Accordingly, a complete view of the vagina and cervix is accomplished with one simple device.

The operation of the preferred embodiment of FIGS. 14–19 is analogous to the operation of the preferred embodiment of FIG. 9.

Figure 14:
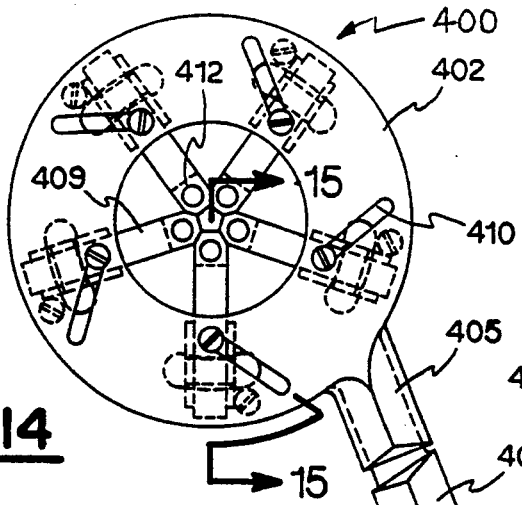
FIG. 14 is a rear, elevational view of the dilator arms and opening and flaring mechanism of another preferred embodiment of the invention, in a closed position.
Figure 15:
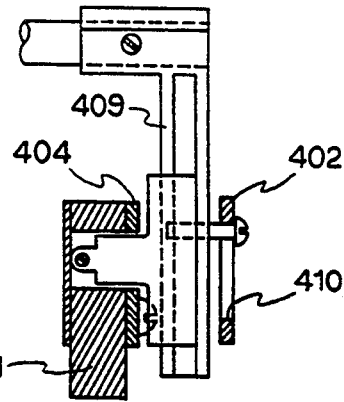
FIG. 15 is a fragmentary, sectional view taken along line 15—15 of FIG. 14, on an enlarged scale.
Figure 16:
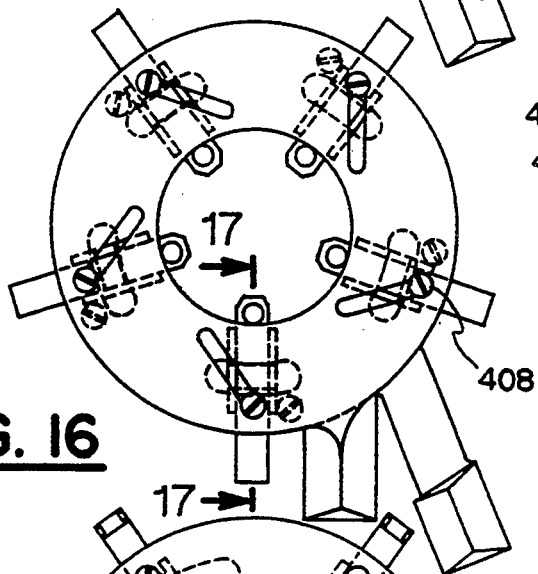
FIG. 16 is a rear, elevational view of the dilator arms and opening and flaring mechanism of the preferred embodiment of the invention shown in FIG. 14, in a open position.
Figure 17:
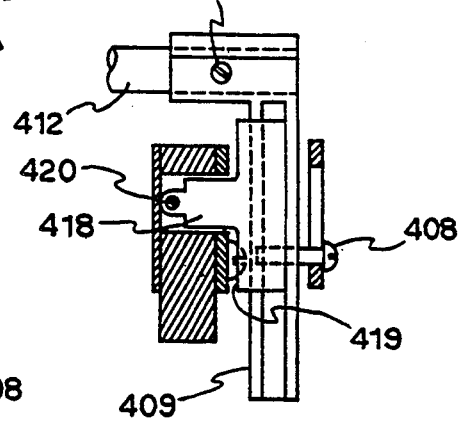
FIG. 17 is a fragmentary, sectional view taken along line 17—17 of FIG. 16, on an enlarged scale.

Dilator 400 is inserted into the body cavity when arms 412 are in the closed position shown in FIGS. 14 and 15. By using relatively small, rod-like arms 412, the collective extent of the five arms 412 shown is small compared to conventional dilators. Rotation of lever 405 from the position shown in FIG. 14 to the further clockwise position shown in FIG. 16 causes arms 412 to move smoothly, radially outwardly to the desired "iris" diameter; that is, to the desired opening size through which the operator looks that is defined by the extents of dilator arms 412.

The radially outward movement of arms 412 is caused by extension 409 moving radially outwardly as iris diameter control disk 402 moves clockwise relative to main body 401 which movement is effected by movement of guide slots 410 relative to guide screws 408. Guide screws 408 are substantially fixed relative to extension 409, whereby extension 409 slides relative to guide member 418 and, hence, relative to main body 401.

Figure 18:
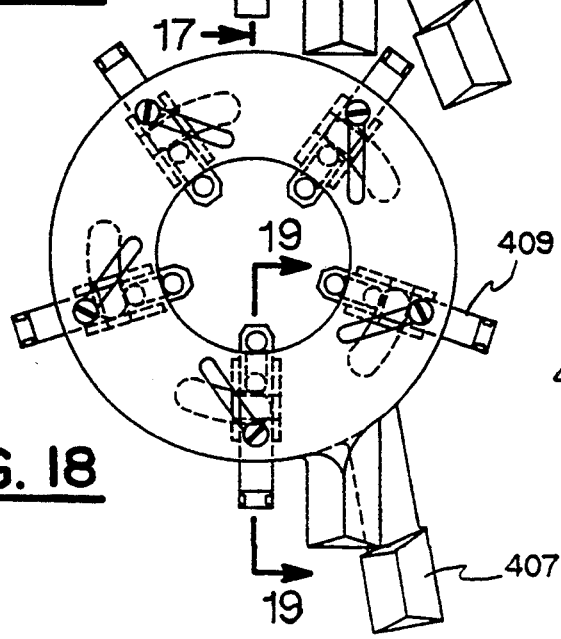
FIG. 18 is a rear, elevational view of the dilator arms and opening and flaring mechanism of the preferred embodiment of the invention shown in FIG. 14, in a open and flared position.

As described above, the pivotable attachment of guide member 418 to main body 401 by means of pivot screw 420 causes guide member 418 to tilt as shown in FIGS. 18 and 19 when clockwise movement of lever 407 brings the head of flare screw 416 into contact with inner surface 419 of guide member 418 as arm flare control disk 404 likewise moves clockwise.

The operation of insertion rod 516 depicted in FIG. 20 is as follows. When used with the preferred embodiments of FIGS. 5, 9, or 14, for example, insertion rod 516 is placed radially inwardly of the rod-like dilator arms, such as represented by dilator arms 512. Hemispherical tip 518 of insertion rod 516 engages the free ends of dilator arms 512, whereby hemispherical tip 518 provides a unified surface for the free ends of dilator arms 512 to render insertion into a body cavity even easier. After insertion to the desired distance, dilator arms 512 are moved radially outwardly to enlarge the body cavity for viewing or for performing the desired medical procedure, the outward movement being accomplished by the movement of schematically illustrated movable member 504 moving away from representative base 502; i.e., to the right as view in FIG. 20. Insertion rod 516 is then completely removed by pulling it to the left as shown in FIG. 20. It is further proposed to make hemispherical tip 518 of a sufficiently soft material so that insertion rod 516 can be removed without opening dilator arms 512 owing to the material of tip 518 conforming to the engaging surfaces of dilator arms 512.

The number of dilator arms is varied dependent on the size of the patient and the intended use. As few as two dilator arms will be used, and up to twelve or more arms will be used in the case of vaginal examination of obese, large, or pregnant women, or woman who have had multiple childbirths.

The material to be used for the dilators according to the invention is preferably sufficiently strong plastic when the dilator is constructed for one-time use.

In the case of reusable dilators, the material will be preferably surgical steel or like materials. It is likewise contemplated that the handle and main body portion of the dilator be made reusable, while the dilator arms and portions which tend to come into close proximity to the body cavity being examined are made of disposable plastic material.

In addition, it is contemplated that the angle between the free ends and the pivotably attached ends of the dilator arms be varied depending on the type of orifice to be examined.

Still further, the dilator arms can be constructed so that the arms comprise a number of detachable segments, whereby the length and/or configuration of the dilator arms can be varied. In such manner, it is contemplated that only the outermost portions of the dilator arms be reusable, dependent on the size and intended use of the dilator. It is contemplated that the dilator arms be configured for use in microsurgery operations, and operations involving incisions in a body wall, such as for hernia operations. Still further, configurations of the dilators arms and the overall size of the dilator will be varied within the scope of the invention to include non-medical uses, such as in veterinary procedures.

As required, disposable plastic sheaths will be placed over not only the handle and main body portion, but also over the dilator arms themselves. It is likewise envisioned that to further facilitate the dilation of the walls of the body cavity in a smooth and even manner, an elastic, expandable, transparent tube can be disposed on the dilator arms. Such a tube may be made of polyisobutyle. This expandable tube functions to protect the body tissue, such as the vaginal walls, from inadvertent contact with diagnostic or surgical instruments and from possible vaporization from the directed laser beams during surgery. The tube may be especially useful when examining or performing surgery on excessively obese patients whose loose flesh extends in between the dilator arms into the field of view.

A ratchet mechanism, or other locking mechanism will be disposed in the handle of the dilator for allowing the physician to maintain the body cavity at any desired degree of dilation when hands-free operation is desired.

Preferably, the overall diameter of the plurality of dilator arms collectively define a cross section which is sufficiently small that all the arms fit inside a conventional tampon applicator when in a closed position.

In the case of vaginal examinations, surgical steel dilator arms will be surrounded by an elastic tubing or sheathing to provide a warmer examination. The plastic sheathing may be made of cellulose, TEFLON TM, or like plastic material. The dilator arms themselves may be constructed of plastic having sufficient elasticity so that unnecessary pressure on the walls of the body cavity is eliminated.

In the case of a dilator having a reusable handle portion, a variety of sets of dilator rods of different lengths and differing dilation angles can be provided for reducing the number of more expensive reusable handle components required, while increasing the number of sizes available for selection by the physician so as to allow the physician to select an optimal combination of dilator arm sizes, dilation angles, and lengths.

The power for illuminating the light source associated with the fiber optics and/or the light transmitting windows can be an independent light source or a light source powered by a battery installed in a portion of the handle or base of the dilator. The battery may be rechargeable, in which case electrical contacts will be provided on the base or handle so that the dilator can be inserted into a recharger when not in use. An AC/DC converter can be used instead of or in conjunction with such rechargeable batteries.

In a like manner, such as through a bendable wire, a camera may be mounted to the dilator.

While this invention has been described as having a preferred design, it is understood that it is capable of further modifications, uses and/or adaptations of the invention following in general the principle of the invention and including such departures from the present disclosure as come within the known or customary practice in the art to which to invention pertains and as may be applied to the central features hereinbefore set forth, and fall within the scope of the invention and of the limits of the appended claims.

We claim:

1. A speculum for dilating a body cavity, said speculum comprising:
   a) a base;
   b) a plurality of arms pivotally attached to said base;
   c) an actuator plate disposed adjacent to and movable relative to said base and to said arms;
   d) means disposed on said actuator plate for engaging each one of said plurality of arms and for moving the arms relative to each other from a closed position to an open position when said actuator plate is moved relative to said base;
   e) said closed position being defined by said plurality of arms being disposed adjacent to each other; and
   f) said open position being defined by said plurality of arms being disposed spaced apart from each other, wherein:
   g) each one of said plurality of arms includes a free end distant from said base; and
   h) an insertion rod is removably disposed inwardly of said plurality of arms.

2. A speculum as defined in claim 1, wherein:
   a) said engaging means moves said actuator plate in a first direction relative to said base for moving said plurality of arms from said closed position to said open position; and
   b) said engaging means moves said actuator plate in a second direction relative to said base for moving said plurality of arms from said open position to said closed position.

3. A speculum as defined in claim 1, wherein:
   a) each one of said plurality of arms includes an elongated rod.

4. A speculum as defined in claim 1, wherein:
   a) each of said plurality of arms includes an attachment portion adjacent to said base and a tissue-dilating portion extending from said attachment portion and disposed spaced apart from said base; and
   b) said tissue-dilating portion extends at an obtuse angle relative to said attachment portion.

5. A speculum as defined in claim 1, wherein:
   a) said plurality of arms includes a dilating blade and a plurality of dilating rods.

6. A speculum as defined in claim 1, wherein:
   a) said plurality of arms includes a dilating blade.

7. A speculum as defined in claim 1, wherein:
   a) said plurality of arms includes a pair of substantially oppositely spaced opposed dilating blades.

8. A speculum as defined in claim 7, wherein:
   a) said plurality of arms includes a pair of substantially oppositely disposed dilating rods.

9. A speculum as defined in claim 7, wherein:
   a) said plurality of arms includes two pairs of substantially oppositely disposed dilating rods.

10. A speculum as defined in claim 1, wherein:
    a) said plurality of arms includes a pair of substantially oppositely spaced opposed dilating blades and a remaining plurality of arms, wherein b) each one of said pair of dilating blades includes a curved free end disposed distant from said base;

c) each one of said remaining plurality of arms includes a free end disposed distant from said base; and d) the curved free ends of said dilating blades are configured to substantially cover said free ends of said remaining plurality of arms when said remaining plurality of arms is in a closed position and said dilating blades are in a closed position.

11. A speculum as defined in claim 1, wherein:

a) a soft, deformable tip is disposed on a free end of said insertion rod distant from said base; and b) said deformable tip is configured for mating with said free ends of said plurality of arms and for defining a blunt insertion tip for insertion into a body cavity.

12. A speculum for dilating a body cavity, said speculum comprising:

a) a base;

b) a plurality of arms pivotally and rotatably attached to said base;

c) means disposed on said base for pivoting and rotating each one of said plurality of arms relative to each other for moving said arms from a closed position to an open position:

d) said closed position being defined by said plurality of arms being disposed adjacent to each other; and e) said open position being defined by said plurality of arms being disposed spaced apart from each other, wherein:

f) said pivoting and rotating means includes an upper actuator disk rotatably attached to said base;

g) means is disposed on said upper actuator disk for pivoting and rotating said plurality of arms while moving said arms from said closed position to said open position;

h) a lower actuator disk is disposed adjacent said upper actuator disk and is rotatably attached to said base; and i) means is disposed on said lower actuator disk for tilting each one of said plurality of arms relative to each other.

13. A speculum as defined in claim 12, wherein:

a) said pivoting and rotating means includes an actuating member movable in a first direction relative to said base for moving said plurality of arms from said closed position to said open position; and b) said actuating member is movable in a second direction relative to said base for moving said plurality of arms from said open position to said closed position.

14. A speculum for dilating a body cavity, said speculum comprising:

a) a base;

a plurality of arms pivotally attached to said base;

c) an actuator, wherein said actuator and said base are perpendicularly movable relative to each other and define a perpendicular distance therebetween;

d) means for adjusting the perpendicular distance between said base and said actuator plate;

e) means disposed on said actuator for engaging each one of said plurality of arms and for moving the arms relative to each other from a closed position to an open position when said actuator and said base are moved relative to each other;

f) said closed position being defined by said plurality of arms being disposed adjacent to each other; and g) said open position being defined by said plurality of arms being disposed spaced apart from each other, h) wherein each of said plurality of arms pivots on said base in a radial direction between said closed position and said open position.

15. A speculum as defined in claim 14, wherein:

a) said plurality of arms includes a pair of substantially oppositely disposed dilating rods.

16. A speculum as defined in claim 14, wherein:

a) said plurality of arms includes a pair of substantially oppositely spaced opposed dilating blades.

17. A speculum as defined in claim 14, wherein:

a) said plurality of arms includes a pair of substantially oppositely spaced opposed dilating blades and a remaining plurality of arms:

b) each one of said pair of dilating blades includes a curved free end disposed distant from said base;

c) each one of said remaining plurality of arms includes a free end disposed distant from said base; and d) the curved free ends of said dilating blades are configured to substantially cover said free ends of said remaining plurality of arms when said plurality of remaining arms is in a closed position and said dilating blades are in a closed position.

18. A speculum as defined in claim 14, wherein:

a) said adjusting means perpendicularly moves said actuator plate in a first direction relative to said base for moving said plurality of arms from said closed position to said open position; and b) said adjusting means perpendicularly moves said actuator plate in a second direction relative to said base for moving said plurality of arms from said open position to said closed position.

19. A speculum as defined in claim 14, wherein:

a) each one of said plurality of arms includes an elongated rod.

20. A speculum as defined in claim 14, wherein:

a) each of said plurality of arms includes an attachment portion adjacent to said base and a tissue-dilating portion extending from said attachment portion and disposed spaced apart from said base; and b) said tissue-dilating portion extends at an obtuse angle relative to said attachment portion.

21. A speculum as defined in claim 14, wherein:

a) said plurality of arms includes a dilating blade and a plurality of dilating rods.

22. A speculum as defined in claim 14, wherein:

a) said plurality of arms includes a dilating blade.

23. A speculum as defined in claim 14, wherein:

a) said plurality of arms are made of plastic.

24. A speculum as defined in claim 14, further comprising:

a) a plurality of plastic sheaths, wherein each of said plurality of plastic sheaths is placed on a corresponding one of said plurality of arms.

25. A speculum as defined in claim 14, further comprising:

a) an expandable tube disposed over said plurality of arms such that when said plurality of arms are in an open position said tube is expanded and protects the body cavity from contacting said plurality of arms.

26. A speculum as defined in claim 14, wherein:

a) said plurality of arms includes two pairs of substantially oppositely disposed dilating rods.

27. A speculum as defined in claim 14, wherein:

a) each one of said plurality of arms includes a free end distant from said base; and
b) an insertion rod is removably disposed inwardly of said plurality of arms.

28. A speculum as defined in claim 27, wherein:
a) a soft, deformable tip is disposed on a free end of said insertion rod distant from said base; and
b) said deformable tip is configured for mating with said free ends of said plurality of rods and for defining a blunt insertion tip for insertion into a body cavity.

29. A speculum as defined in claim 1, wherein:
a) said plurality of arms are made of plastic.

30. A speculum as defined in claim 1, further comprising:
a) a plurality of plastic sheaths, wherein each of said plurality of plastic sheaths is placed on a corresponding one of said plurality of arms.

31. A speculum as defined in claim 1, further comprising:
a) an expandable tube disposed over said plurality of arms such that when said plurality of arms are in an open position said tube is expanded and protects the body cavity from contacting said plurality of arms.

* * * * *